(12) United States Patent
Uhr

(10) Patent No.: US 9,420,791 B2
(45) Date of Patent: Aug. 23, 2016

(54) BIOCIDAL COMPOSITIONS

(75) Inventor: Hermann Uhr, Leverkusen (DE)

(73) Assignee: LANXESS Deutschland GmbH, Cologne (DE)

( * ) Notice: Subject to any disclaimer, the term of this patent is extended or adjusted under 35 U.S.C. 154(b) by 758 days.

(21) Appl. No.: 13/382,563

(22) PCT Filed: Jul. 6, 2010

(86) PCT No.: PCT/EP2010/059637
§ 371 (c)(1),
(2), (4) Date: Dec. 18, 2012

(87) PCT Pub. No.: WO2011/003906
PCT Pub. Date: Jan. 13, 2011

(65) Prior Publication Data
US 2013/0090361 A1    Apr. 11, 2013

(30) Foreign Application Priority Data

Jul. 7, 2009 (EP) ..................................... 09164779

(51) Int. Cl.
| A01N 43/80 | (2006.01) |
| A61K 31/30 | (2006.01) |
| A61K 31/425 | (2006.01) |
| A01N 59/16 | (2006.01) |

(52) U.S. Cl.
CPC .............. *A01N 43/80* (2013.01); *A61K 31/30* (2013.01); *A61K 31/425* (2013.01)

(58) Field of Classification Search
CPC .............................. A01N 43/80; A01N 59/20
See application file for complete search history.

(56) References Cited

U.S. PATENT DOCUMENTS

| 5,073,582 A | 12/1991 | LeSota |
| 5,461,150 A | 10/1995 | Gironda et al. |
| 5,910,503 A | 6/1999 | Mattox et al. |
| 6,255,331 B1 | 7/2001 | El A'mma et al. |
| 6,361,788 B1 | 3/2002 | Antoni-Zimmermann et al. |
| 6,635,305 B2 | 10/2003 | Sirejacob |
| 8,414,931 B2 | 4/2013 | Patel |
| 2002/0164266 A1* | 11/2002 | Wachtler et al. ............... 422/37 |
| 2003/0004198 A1 | 1/2003 | Still et al. |
| 2006/0127272 A1 | 6/2006 | Saitmacher et al. |
| 2008/0076803 A1* | 3/2008 | Beilfuss et al. .............. 514/345 |

FOREIGN PATENT DOCUMENTS

| DE | 10319966 A1 * | 12/2004 |
| EP | 0749689 A2 | 12/1996 |
| EP | 749689 A2 * | 12/1996 |
| EP | 0910952 A1 | 4/1999 |
| EP | 0913090 A1 | 5/1999 |
| EP | 0983723 A1 | 3/2000 |
| EP | 1044609 A1 | 10/2000 |
| EP | 1120040 A2 | 8/2001 |
| EP | 1369461 A1 | 12/2003 |
| JP | 02304005 | 12/1990 |
| WO | 9908530 A1 | 2/1999 |

OTHER PUBLICATIONS

Pelletier et al (International Journal of Molecular Science, Jul. 2009, vol. 10, pp. 3209-3223).*
European Search Report dated Dec. 7, 2009 for EP09164779.
Pelletier, E., "Biofouling Growth in Cold Estuarine Waters and Evaluation of Some Chitosan and Copper Anti-Fouling Paints", Int. J. Mol. Sci. 2009, 10, pp. 3209-3223.

* cited by examiner

*Primary Examiner* — Sean Basquill
*Assistant Examiner* — Mark V Stevens

(57) ABSTRACT

The present invention relates to storage-stable biocidal compositions comprising at least one halogen-free isothiazolinone such as in particular 2-methyl-2H-isothiazol-3-one (MIT) and/or 1,2-benzisothiazolin-3-one (BIT) and/or salts thereof, and also stabilizing amounts of copper(II) ions, to a method for preserving technical materials by means of the aforementioned biocidal compositions, and to the technical materials treated therewith.

10 Claims, No Drawings

BIOCIDAL COMPOSITIONS

CROSS REFERENCE TO RELATED PATENT APPLICATIONS

The present patent application claims the right of priority under 35 U.S.C. §119 (a)-(d) and 35 U.S.C. §365 of International Application No. PCT/EP2010/59637, filed Jul. 6, 2010, which was published in German as International Patent Publication No. WO 2010/003906 A2 on Jan. 16, 2011, which is entitled to the right of priority of European Patent Application No. EP 09164779.2 filed on Jul. 7, 2009.

The present invention relates to storage-stable biocidal compositions comprising at least one halogen-free isothiazolinone such as in particular 2-methyl-2H-isothiazol-3-one (MIT) and/or 1,2-benzisothiazolin-3-one (BIT) and/or salts thereof, and also stabilizing amounts of copper(II) ions, to a method for preserving technical materials by means of the aforementioned biocidal compositions, and to the technical materials treated therewith.

The literature describes various methods for protecting isothiazolinones against chemical decomposition. These are essentially the stabilization of 3:1 mixtures of 5-chloro-2-methyl-4-isothiazolin-3-one (CMIT) and MIT, as are typically produced during the industrial preparation.

CMIT, which has a tendency towards decomposition, has to be stabilized, whereas MIT is stable under conditions typical during use or storage.

EP 0 721 736 A describes stabilized Isothiazolinone solutions of CMIT and MIT in which the stabilization is achieved by non-chelated copper(II) ions, where the weight ratio of copper(II) ions and isothiazolinones is between 0.0008:1.5 and 0.02:1.5.

Furthermore, EP 0 749 689 A describes the prevention of precipitates in isothiazolinone formulations through the use of copper(II) ions and metal nitrates. Here, 0.1 to 25% of metal nitrates, such as, for example, magnesium nitrate, and ca. 0.1 to 100 ppm of copper(II) ions are used for the stabilization.

It is already known from EP 1 369 461 A that the degradation of isothiazolinones in aqueous paint systems can be slowed by using 1 to 200 ppm of copper(II) ions for the stabilization. Relative to the isothiazolinone used, the amounts of copper here are comparatively high.

EP 0 408 215 describes non-wood penetrating, isothiazolinone-containing paints which are stabilized by water-insoluble copper compounds, such as, for example, copper salts of fatty acids. Furthermore, it is known from EP 1 044 609 A, EP 0 910 952 and EP 0 913 090 A to use copper salts as co-stabilizers alongside large amounts of strong oxidizing agents such as, for example, iodates, periodates, chlorates, perchlorates and organic oxidizing agents.

On account of the above-described stability of MIT and also BIT, a stabilization of biocidal compositions comprising MIT or BIT individually or in combination is typically not required (see also EP 1 005 271 A).

However, more recent investigations have shown that in the case of biocidal compositions comprising halogen-free isothiazolinones such as, for example, biocidal compositions comprising BIT and MIT, upon storage at elevated temperatures, as are often encountered for example in subtropical or tropical climates, considerable discolorations, degradation of the active ingredients and precipitations can result.

It was therefore the object to avoid these disadvantages.

Biocidal compositions have now been found which comprise
one or more isothiazolinones, where the biocidal compositions, based on their total weight fraction of isothiazolinones, comprise to at least 98.0%, preferably to at least 99.0%, particularly preferably to at least 99.5% and very particularly preferably exclusively, those isothiazolinones which are halogen-free and
1 to 500, preferably 5 to 500, particularly preferably 10 to 300, ppm by weight of copper(II) ions, based on the total weight fraction of the isothiazolinone or isothiazolinones in the biocidal composition.

It may be noted at this point that the scope of the invention encompasses all desired and possible combinations of the components, value ranges and/or process parameters stated above and below, in general terms or in preferred ranges.

In one preferred embodiment, the biocidal compositions comprise two or more isothiazolinones, particularly preferably two isothiazolinones.

In a further preferred embodiment, the biocidal compositions comprise one or more isothiazolinones, preferably two or more isothiazolinones, particularly preferably two isothiazolinones, where the biocidal compositions, based on their total weight fraction of isothiazolinones, comprise to at least 98.0%, preferably to at least 99.0%, particularly preferably to at least 99.5% and very particularly preferably exclusively, those isothiazolinones which are selected from the group: 2-methyl-2H-isothiazol-3-one; 1,2-benzisothiazolin-3-one or salts thereof; 2-n-octyl-4-isothiazolin-3-one, N-butyl-1,2-benzisothiazolin-3-one and 2-methyl-4,5-trimethylene-4-isothiazolin-3-one.

Preference is given to isothiazolinones which are selected from the group 2-methyl-2H-isothiazol-3-one; 1,2-benzisothiazolin-3-one or salts thereof and 2-n-octyl-4-isothiazolin-3-one.

Very particularly preferably, the biocidal compositions comprise as isothiazolinones only 2-methyl-2H-isothiazol-3-one and 1,2-benzisothiazolin-3-one and/or salts thereof.

The biocidal compositions according to the invention are preferably liquid. The term "liquid biocidal composition" within the context of the invention means that the composition is present in the liquid state at room temperature and the content of solid constituents is 0 to 1% by weight, preferably 0 to 0.5% by weight. The liquid biocidal compositions are particularly preferably free from solid constituents.

The liquid biocidal compositions can be aqueous or nonaqueous, nonaqueous biocidal compositions within the context of the invention being understood as meaning those which, based on the total weight of the biocidal compositions, have a fraction of less than 5% by weight, preferably a fraction of less than 2% by weight, of water.

The weight fraction of isothiazolinones in the biocidal compositions can be for example 0.1 to, rounded on account of the required copper fraction, 100%. Particularly when using 2-n-octyl-4-isothiazolin-3-one which is liquid at room temperature, very high to maximum fractions of isothiazolinones can be realized even in the form of liquid biocidal compositions.

In the case of aqueous, liquid biocidal compositions, a weight fraction of isothiazolinones in the biocidal compositions of from 0.1 to 50% by weight is preferred, a weight fraction of from 3 to 20% by weight is particularly preferred, a fraction of from 5 to 15% by weight is very particularly preferred.

Within the context of the invention, liquid, aqueous biocidal compositions are very particularly preferred.

In one embodiment, the biocidal compositions can further comprise at least one oxidizing agent which is selected from the group: iodate, periodate, perchlorate, chlorate, bromate, organic oxidizing agents, where iodate, periodate and bromate are preferred and iodate is particularly preferred. The aforementioned inorganic oxidizing agents can be incorporated into the biocidal compositions in a manner known per se, for example in the form of their alkali metal salts.

The content of at least one oxidizing agent in the biocidal compositions can be for example 50 to 10 000, preferably 100 to 1000, particularly preferably 10 to 300 ppm by weight, based on their weight content of isothiazolinones.

In a preferred embodiment, the biocidal compositions are free from the aforementioned oxidizing agents, which, within the context of the invention, means a content of less than 2 ppm by weight, preferably complete absence of the oxidizing agents, based on the biocidal compositions.

Preferred liquid aqueous biocidal compositions are those which are essentially free from organic solvents. Within the context of the invention, essentially free from organic solvents means a weight fraction of organic solvents in the biocidal compositions of from 0 to 3% by weight, preferably 0 to 1% by weight, preferably complete absence of organic solvents, where the isothiazolinones are not regarded as organic solvent even if they are liquid.

In a preferred embodiment, the biocidal compositions have a nitrate content of 1000 ppm by weight or less, preferably of 250 ppm by weight or less, particularly preferably 50 ppm by weight or less, based on the total weight of the biocidal compositions. In another embodiment, the nitrate content of the biocidal compositions is less than 20 ppm by weight.

Preferred liquid, aqueous biocidal compositions are those which comprise two isothiazolinones, where the isothiazolinones are 2-methyl-2H-isothiazol-3-one (MIT) and 1,2-benzisothiazolin-3-one (BIT) or salts thereof and which further comprise 1 to 500, preferably 5 to 500, particularly preferably 10 to 300, ppm by weight of copper(II) ion, based on the weight fraction of the aforementioned isothiazolinones in the biocidal composition.

These preferred liquid, aqueous biocidal compositions comprise preferably 0.5 to 20% by weight of BIT or salts thereof, in each case calculated on the basis of free BIT, preferably 1 to 15% by weight and 0.5 to 20% by weight of MIT, preferably 1 to 15% by weight of MIT.

The weight ratio of BIT to MIT can vary within a broad range, preferably, the weight ratio of BIT to MIT is 1:10 to 10:1, preferably 1:5 to 5:1.

Preferably, the aforementioned liquid, aqueous biocidal compositions are essentially free from organic solvents.

BIT is preferably used in the form of its alkali metal salts, for example in the form of the lithium salt, sodium salt or potassium salt. The alkali metal salts of BIT are usually prepared by reacting BIT with the corresponding alkali metal hydroxide, where typically 0.7 to 1.2 mol equivalents of the alkali metal hydroxide, based on BIT, preferably 0.8 to 1.1 mol equivalents, are used The preferred liquid, aqueous biocidal compositions when using BIT salts typically then have a pH of from 7 to 11 under standard conditions, preferably a pH of from 8 to 10.

The biocidal compositions according to the invention are particularly suitable for preserving technical materials which are susceptible to infestation by microorganisms.

The invention therefore further relates to the use of the biocidal compositions according to the invention for protecting technical materials against infestation by and the control of microorganisms, and also to a method for protecting technical materials against infestation and/or destruction by microorganisms, which is characterized in that the biocidal compositions according to the invention are allowed to act on the microorganism or its habitat. The action can take place here in diluted or undiluted form.

The invention moreover relates to technical materials obtainable by treating technical materials with the biocidal compositions according to the invention, and also to technical materials comprising one or more isothiazolinones, where the technical materials, based on their total weight fraction of isothiazolinones, comprise to at least 98.0%, preferably to at least 99.0%, particularly preferably to at least 99.5% and very particularly preferably exclusively, those isothiazolinones which are halogen-free and 1 to 500, preferably 5 to 500, particularly preferably 10 to 300, ppm by weight of copper(II) ions, based on the total weight fraction of the isothiazolinone or isothiazolinones in the technical material.

Preferred technical materials are functional liquids and water-containing technical products, such as, for example:

paints, colours, plasters and other coating compositions starch solutions and slurries or other products prepared on the basis of starch, such as, for example, printing thickeners slurries of other raw materials, such as, for example, chromatic pigments, such as, for example, iron oxide pigments, carbon black pigments, titanium dioxide pigments, or slurries of inorganic fillers and pigments such as kaolin, calcium carbonate, gypsum, bentonite, magnesium silicates, smectite or talc.

construction chemical products such as, for example, concrete additives, for example based on molasses, lignosulphonate or polyacrylates, bitumen emulsions or sealants;

sizes or adhesives based on known animal, vegetable or synthetic raw materials;

polymer dispersions based on, for example, polyacrylates, polystyrene-acrylates, styrene-butadiene, polyvinyl acetates;

detergents and cleaners for industry and domestic use mineral oils and mineral oil products such as, for example, diesel fuels cooling lubricants for metal processing, for example based on mineral oil-containing, semisynthetic or synthetic concentrates auxiliaries for the leather, textile or photochemical industry precursors and intermediates of the chemical industry, for example during dye production and storage inks or washes waxes and clay emulsions.

Microorganisms within the context of the invention are, for example, bacteria, mildew, yeasts and slime organisms. By way of example but without limitation thereto, mention may be made of the following microorganisms:

*Alternaria* such as *Alternaria tenuis*, *Aspergillus* such as *Aspergillus niger*, *Chaetomium* such as *Chaetomium globosum*, *Fusarium* such as *Fusarium solani*, *Lentinus* such as *Lentinus tigrinus*, *Penicillium* such as *Penicillium glaucum*, *Polyporus*, such as *Polyporus versicolor*, *Aureobasidium*, such as *Aureobasidium pullulans*, *Sclerophoma*, such as *Sclerophoma pityophila*, *Trichoderma*, such as *Trichoderma viride*.

*Alcaligenes* such as *Alcaligenes faecalis*, *Bacillus* such as *Bacillus subtilis*, *Escherichia* such as *Escherichia coli*,

*Pseudomonas* such as *Pseudomonas aeruginosa* or *Pseudomonas fluorescens, Staphylococcus* such as *Staphylococcus aureus*;

*Candida* such as *Candida albicans, Geotrichum* such as *Geotrichum candidum, Rhodotorula* such as *Rhodotorula rubra*.

As well as the isothiazolinones, the biocidal compositions according to the invention can comprise at least one further biocidal active ingredient which is not an isothiazolinone, where the further biocidal active ingredients may be algaecides, fungicides or bactericides.

Preferred algaecides are triazine compounds, such as, for example, terbutryn, cybutryn, propazine or terbutone; urea compounds, such as, for example, diuron, benzthiazuron, isoproturon, methabenzthiazuron and tebuthiuron or uracils, such as, for example, terbacil.

Preferred fungicides are azaconazole, bromuconazole, cyproconazole, dichlobutrazole, diniconazole, hexaconazole, metaconazole, penconazole, propiconazole, tebuconazole, methfuroxam, carboxin, fenpiclonil, butenafin, imazalil, thiabendazole, 1-hydroxy-2-pyridine-thione, and also their Cu, Na, Fe, Mn, Zn salts; tetrachloro-4-methylsulphonylpyridine, 3-iodo-2-propinyl n-butylcarbamate, bethoxazin, 2,4,5,6-tetrachlorophthalodinitrile, triadimefon and carbendazim.

Preferred bactericides are: glutaraldehyde, pyrithion and its salts, 2-bromo-2-nitro-1,3-propanediol, o-phthaldialdehyde, 2,2-dibromo-3-nitrilepropionamide, 1,2-dibromo-2,4-dicyanobutane, p-hydroxybenzoic acid, chlorophene, 3-methyl-4-chlorophenol, o-phenylphenol, p-tert-amylphenol, quaternary ammonium salt such as, for example, benzalconium chloride, benzyldimethyltetradecylammonium chloride, benzyldimethyldodecylammonium chloride, dichlorobenzyldimethylalkylammonium chloride, didecyldimethylammonium chloride, dioctyldimethylammonium chloride, N-hexadecyltrimethylammonium chloride, N-cyclohexyl-diazenium dioxide potassium salt, formaldehyde or formaldehyde depot substances such as, for example, N-(2-hydroxypropyl)aminomethanol, benzyl alcohol (hemi)formal, N-methylol-chloroacetamide, 1,3-bis(hydroxymethyl)-5,5-dimethylimidazolidine-2,4-dione (DMDMH), tetramethylolacetylenediurea (TMAD), ethylene glycol hemiformal, ethylene glycol bis-hemiformal, hexahydro-s-triazine, 7-ethylbicyclooxazolidine, 3,3'-methylene[5-methylbisoxazolidine], dimethylolurea, N-methylolurea, methylenebismorpholine, sodium N-(hydroxymethyl)glycinate.

If the biocidal compositions according to the invention comprise at least one further biocidal active ingredient as well as the isothiazolinones, in the case of aqueous biocidal compositions, preference is given to the following biocides:

Formaldehyde donors such as, for example, benzyl hemiformal, tetramethylolacetylenediurea (TMAD), 1,3-bis(hydroxymethyl)-5,5-dimethylimidazolidine-2,4-dione (DMDMH), dimethylolurea, N-methylolurea, ethylene glycol hemiformal, ethylene glycol bis-hemiformal, phenols such as, for example, p-chloro-m-cresol, p-tert-amylphenol, o-phenylphenol, chlorophene, quaternary ammonium salts, such as, for example, benzalkonium chloride, benzyldimethyltetradecylammonium chloride, benzyldimethyldodecylammonium chloride, dichlorobenzyldimethylalkylammonium chloride, didecyldimethylammonium chloride, dioctyldimethylammonium chloride, N-hexadecyltrimethylammonium chloride, and N-cyclohexyldiazonium dioxide potassium salt and 2-dibromo-2,4-dicyanobutane.

In a particularly preferred embodiment of the invention, the biocidal compositions according to the invention comprise no further biocides besides the isothiazolinones.

The use concentrations of the biocidal compositions according to the invention is governed by the type and the occurrence of the microorganisms to be controlled, of the initial microbial burden and also by the composition of the technical material to be protected. The optimum use amount for a certain application can be ascertained easily in the laboratory by means of test series in a manner known per se and known sufficiently to the person skilled in the art. In general, the use concentrations are in the range from 0.01 to 5% by weight, preferably from 0.05 to 1.0% by weight, of the biocidal compositions according to the invention, based on the material to be protected.

The particular advantage of the invention is that even with the smallest amounts of copper(II) ions, a long-term stability of the biocidal compositions according to the invention can be achieved, and, compared to unstabilized biocidal compositions, active ingredient degradation, discoloration and precipitation of decomposition products can be effectively suppressed, or at least significantly reduced.

EXAMPLES

Example 1

Solution A (Unstabilized)

569.8 g of demineralized water were introduced as initial charge, admixed with 17.86 g of an aqueous sodium hydroxide solution (50% by weight) and 21.6 g of sodium chloride and the mixture was stirred until everything had dissolved. To this was added 41.6 g of BIT (86.5% by weight, manufacturer I), which was made dust-free with water and the mixture was stirred at room temperature until everything had dissolved. Then, with stirring, 69.1 g of an aqueous MIT solution (52.10% by weight) were added to this solution. This gave a clear, virtually colourless solution with a pH of 8.6.

Solution B (Stabilized)

92.86 g of solution A described above were introduced as initial charge and admixed with 7.14 g of a 0.001 molar solution of copper(II) nitrate with stirring. This gave a clear, colourless solution with a pH of 8.6.

Both solutions were stored in each case at 20° C. and 65° C. and in each case the appearance was assessed after 7 days. The results are given in Table 1.

TABLE 1

|  | Solution A (unstabilized) | | Solution B (stabilized) | |
| --- | --- | --- | --- | --- |
|  | 7 days at 20° C. | 7 days at 65° C. | 7 days at 20° C. | 7 days at 65° C. |
| Appearance | Colourless, clear solution | Virtually black solution with yellow sediment | Colourless, clear solution | Colourless, clear solution |

Example 2

Solution C (Unstabilized)

569.5 g of demineralized water were introduced as initial charge and admixed with 17.86 g of aqueous sodium hydroxide solution (50% by weight) and 21.6 g of sodium chloride and the mixture was stirred until everything had dissolved. To this was added 42.0 g of BIT (85.74% by weight, manufacturer II), which was made dust-free with water, and the mixture was stirred at room temperature until everything had dissolved. Then, with stirring, 69.1 g of an aqueous MIT solution (52.10% by weight) were added to this solution. This gave a clear, virtually colourless solution with a pH of 8.8.

Solution D (Stabilized)

92.86 g of solution A described above were introduced as initial charge and admixed with 7.14 g of a 0.001 molar solution of copper(II) nitrate with stirring.

This gave a clear, colourless solution with a pH of 8.8.

Both solutions were stored in each case at 20° C. and 65° C. and in each case the appearance was evaluated after 7 days. The results are shown in Table 2.

TABLE 2

|  | Solution C (unstabilized) | | Solution D (stabilized) | |
| --- | --- | --- | --- | --- |
|  | 7 days at 20° C. | 7 days at 65° C. | 7 days at 20° C. | 7 days at 65° C. |
| Content of BIT (% by wt.) | 4.6% | 3.3% | 4.3% | 4.2% |
| Content of MIT (% by wt.) | 4.8% | 2.8% | 4.5% | 4.4% |
| Appearance | Colourless, clear solution | Dark brown solution with yellow sediment | Colourless, clear solution | Colourless, clear solution |

What is claimed is:

1. Biocidal compositions comprising:
   1% to 15% by weight of at least one isothiazolinone selected from 2-methyl-2H-isothiazol-3-one and salts of 2-methyl-2H-isothiazol-3-one,
   1% to 15% by weight of at least one isothiazolinone selected from 1,2-benzisothiazolin-3-one and salts of 1,2-benzisothiazolin-3-one,
   1 to 500 ppm by weight copper (II) ions, based on the total weight fraction of the isothiazolinones in the biocidal composition,
   wherein one source of the copper (II) ions is copper (II) nitrate,
   and wherein the compositions are aqueous.

2. The biocidal compositions according to claim 1, wherein
   a weight ratio of the at least one isothiazolinone selected from 2-methyl-2H-isothiazol-3-one and salts of 2-methyl-2H-isothiazol-3-one to the at least one isothiazolinone selected from 1,2-benzisothiazolin-3-one and salts of 1,2-benzisothiazolin-3-one is 1:10 to 10:1.

3. The biocidal compositions according to claim 2, wherein the biocidal compositions are essentially free of organic solvents.

4. The biocidal compositions according to claim 3, further comprising at least one oxidizing agent selected from the group consisting of: iodate, periodate, perchlorate, chlorate, bromate and organic oxidizing agents.

5. The biocidal compositions according claim 1, wherein the biocidal compositions are free from iodate, periodate, perchlorate, chlorate, bromate and organic oxidizing agents.

6. The biocidal compositions according to claim 4, wherein the nitrate content of 1000 ppm by weight or less, based on the total weight of the biocidal compositions.

7. The biocidal compositions according to claim 6, wherein, besides the isothiazolinones, the biocidal compositions contain no further biocides.

8. A method of using biocidal compositions according to claim 1 for protecting technical materials against infestation by and the control of microorganisms, the method comprising incorporating the biocidal material into or onto the technical material.

9. A method for protecting technical materials against infestation and/or destruction by microorganisms, the method comprises incorporating biocidal compositions according to claim 1 into or onto the technical material to allow the biocidal compositions to act on the microorganism or its habitat.

10. Technical materials comprising the biocidal compositions according to claim 1.

* * * * *